(12) United States Patent
Morrow

(10) Patent No.: US 8,273,040 B1
(45) Date of Patent: Sep. 25, 2012

(54) ATTITUDE ADJUSTABLE ARM SLING

(76) Inventor: Ramoned Morrow, Baton Rouge, LA (US)

( * ) Notice: Subject to any disclaimer, the term of this patent is extended or adjusted under 35 U.S.C. 154(b) by 196 days.

(21) Appl. No.: 12/592,654

(22) Filed: Dec. 1, 2009

Related U.S. Application Data

(60) Provisional application No. 61/118,660, filed on Dec. 1, 2008.

(51) Int. Cl.
*A61F 5/00* (2006.01)
(52) U.S. Cl. .......................................................... 602/4
(58) Field of Classification Search .................. 602/4, 5, 602/20; 128/877–879; 5/646, 648, 630, 5/922, 933, 636; 2/16, 17
See application file for complete search history.

(56) References Cited

U.S. PATENT DOCUMENTS

| 2,088,927 | A | | 8/1937 | Roy | |
|---|---|---|---|---|---|
| 3,433,221 | A | | 3/1969 | Kendall et al. | |
| 4,285,337 | A | | 8/1981 | Cosentino | |
| 4,372,301 | A | | 2/1983 | Hubbard et al. | |
| 4,572,172 | A | | 2/1986 | Williams | |
| 4,759,353 | A | | 7/1988 | Melendez et al. | |
| 4,834,082 | A | * | 5/1989 | Ghadiali | 602/4 |
| 5,334,132 | A | * | 8/1994 | Burkhead | 602/4 |
| 5,772,617 | A | | 6/1998 | Lay | |
| 6,659,971 | B2 | * | 12/2003 | Gaylord | 602/4 |
| D504,518 | S | | 4/2005 | Diaz et al. | |
| 7,189,213 | B1 | * | 3/2007 | Weber | 602/20 |
| 7,563,236 | B2 | * | 7/2009 | Kazmierczak et al. | 602/4 |
| 2003/0187373 | A1 | * | 10/2003 | Gaylord | 602/4 |
| 2009/0050159 | A1 | | 2/2009 | Jamerson et al. | |

* cited by examiner

*Primary Examiner* — Michael A. Brown
(74) *Attorney, Agent, or Firm* — Patent Law & Venture Group; Gene Scott

(57) ABSTRACT

An arm sling provides elastic elongation to accommodate arms of differing lengths. Wedge shaped blocks are engagable with the sides of the sling to provide abduction of the sling. The sling is made predominantly of a net material so as to provide air circulation around the supported arm. An elastic sheet material supports the hand of the supported arm. A shoulder strap provides a movable cushioned pad for comfortable use of the sling as held by the strap.

7 Claims, 3 Drawing Sheets

ATTITUDE ADJUSTABLE ARM SLING

CROSS-REFERENCE TO RELATED APPLICATIONS

This application is a non-provisional application describing the same invention as an active provisional application Ser. No. 61/118,660, filed on Dec. 1, 2008, and being filed within one year, hereby claims date priority therefrom.

BACKGROUND OF THE INVENTION

1. Field of the Present Disclosure

This disclosure relates generally to supports for engaging a part or portion of the human anatomy and more particularly to an arm sling capable of orienting a supported arm in a preferred attitude relative to the torso.

2. Description of Related Art Including Information Disclosed Under 37 CFR 1.97 and 1.98

Slings for supporting injured arms or shoulders are well known in the prior art. For instance Roy U.S. Pat. No. 2,088,927 discloses an open sling with a cord extending through hems along both sides with loops at both ends which when placed around the neck are able to support an arm as shown in FIG. 1. Other open slings are disclosed in Diaz et al D504518, Cosentino U.S. Pat. No. 4,285,337, Hubbard et al U.S. Pat. No. 4,372,301, Melendez et al U.S. Pat. No. 4,759,353, Lay U.S. Pat. No. 5,772,617, and Jamerson et al 2009/0050159. The open sling appears to be the conventional approach primarily because it allows the injured arm to be easily placed into the sling with the least amount of handling. Kendall et al U.S. Pat. No. 3,433,221 discloses a partially closed (tubular) sling that is designed for enclosing a shoulder as well as its related arm. Williams U.S. Pat. No. 4,572,172 discloses an open sling that may be closed after placement of the arm. Several straps bring the two upper edges of the sling into close proximity to better fit the sling to the arm and to limit the arms motion.

The related art briefly described above discloses arm slings that provide the benefit of supporting an injured arm. In order to place the injured arm into these slings, they are formed as open topped V-shaped flexible or semi-flexible structures. These slings are generally held near the wrist end by a neck strap as shown in Williams, FIG. 1, or a modified neck and shoulder strap, as shown in Hubbard et al FIG. 3. The elbow end of the sling is frequently secured in various ways as also illustrated in Hubbard et al where a waist strap is used. Closure of the top or part of the top of the sling may be in accordance with Cosentino where the neck strap also is used to pull the wrist ends of the sling together, or by separate straps as in Williams. The prior art, as shown by Williams and Hubbard et al does teach the benefits of tightening the sling around the supported arm and more securely holding the sling close to the body. The prior art does not teach an arm sling and securing strap arrangement that has the ability to quickly change the angle that the sling makes with respect to the torso. Actually, it often is desirable to change the position of the supported arm from hour to hour or day to day if supporting the arm in one position for long periods results in detriment to the healing process or becomes uncomfortable to the patient. The present disclosure distinguishes over the prior art providing heretofore unknown advantages as described in the following summary.

BRIEF SUMMARY OF THE INVENTION AND OBJECTIVES

This disclosure teaches certain benefits in construction and use which give rise to the objectives described below. The present invention is an arm supporting apparatus having a V-shaped sling, a shoulder strap, and one or more positioning wedges. The sling is of a net fabric configured contiguously as a pair of side walls joined with a bottom wall and a rear wall forming an open top extending from the rear wall to the front of the apparatus. The net fabric joins an elastic sheet at the front of the apparatus where a patient's hand will rest. The net fabric is able to elongate to accommodate arms of different lengths. A first strap attachment is engaged with the net fabric at the rear wall and extends upwardly from the sling. A second strap attachment is engaged with the side walls of the net fabric and bridges across the open top. One end of the shoulder strap joins the first strap attachment medially, while an opposing end of the shoulder strap joins the second strap attachment. The exterior surface of each of the side walls of the sling have an attachment device mounted thereon. The positioning wedge also has an attachment device mounted on it and these attachment devices, preferably hook and loop surface fastening material, enables the wedge to be mounted onto one or the other of the sides of the sling.

By inserting the positioning wedge between the sling and the torso the supported arm is able to be selectively positioned relative to the body. The supported arm may be positioned away from the body, i.e., rotated upwardly in anterior abduction, or outwardly in lateral abduction. Therefore, the invention presently disclosed distinguishes over the prior art providing benefits to the patient.

The present invention provides immobilization for rotator cuff repairs, anterior repairs, posterior dislocations, capsular shifts, AC sprains, global shoulder instability, problems related to over use, and other shoulder problems.

A primary objective of the present invention is to support a human arm that must be held immobile during healing. Another objective is to provide such an invention as a sling that is able to elongate or shorten to receive arms of differing lengths, as for instance arms of men, women and children. A further objective is to provide a shoulder strap to engage the sling and hold it in a preferred position next to, or adjacent to, the torso. A still further objective is to provide a means for adjusting the orientation or attitude of the sling and to readjust the orientation or attitude easily. Other features and advantages of the present invention will become apparent from the following more detailed description, taken in conjunction with the accompanying drawings, which illustrate, by way of example, the principles of the presently described apparatus and method of its use.

BRIEF DESCRIPTION OF THE SEVERAL VIEWS OF THE DRAWING(S)

Illustrated in the accompanying drawing(s) is an example of the present invention. In such drawing(s):

DETAILED DESCRIPTION OF THE INVENTION

The above described drawing figures illustrate the present invention in a preferred embodiment. Those with ordinary skill in this art may be able to make alterations and modifications to what is described herein without departing from the spirit and scope of this invention. Therefore, it should be understood that what is illustrated is set forth only for the purpose of example and should not be taken as a limitation on the types and numbers of modifications possible within the scope of the present apparatus and its method of use.

Figure 1:
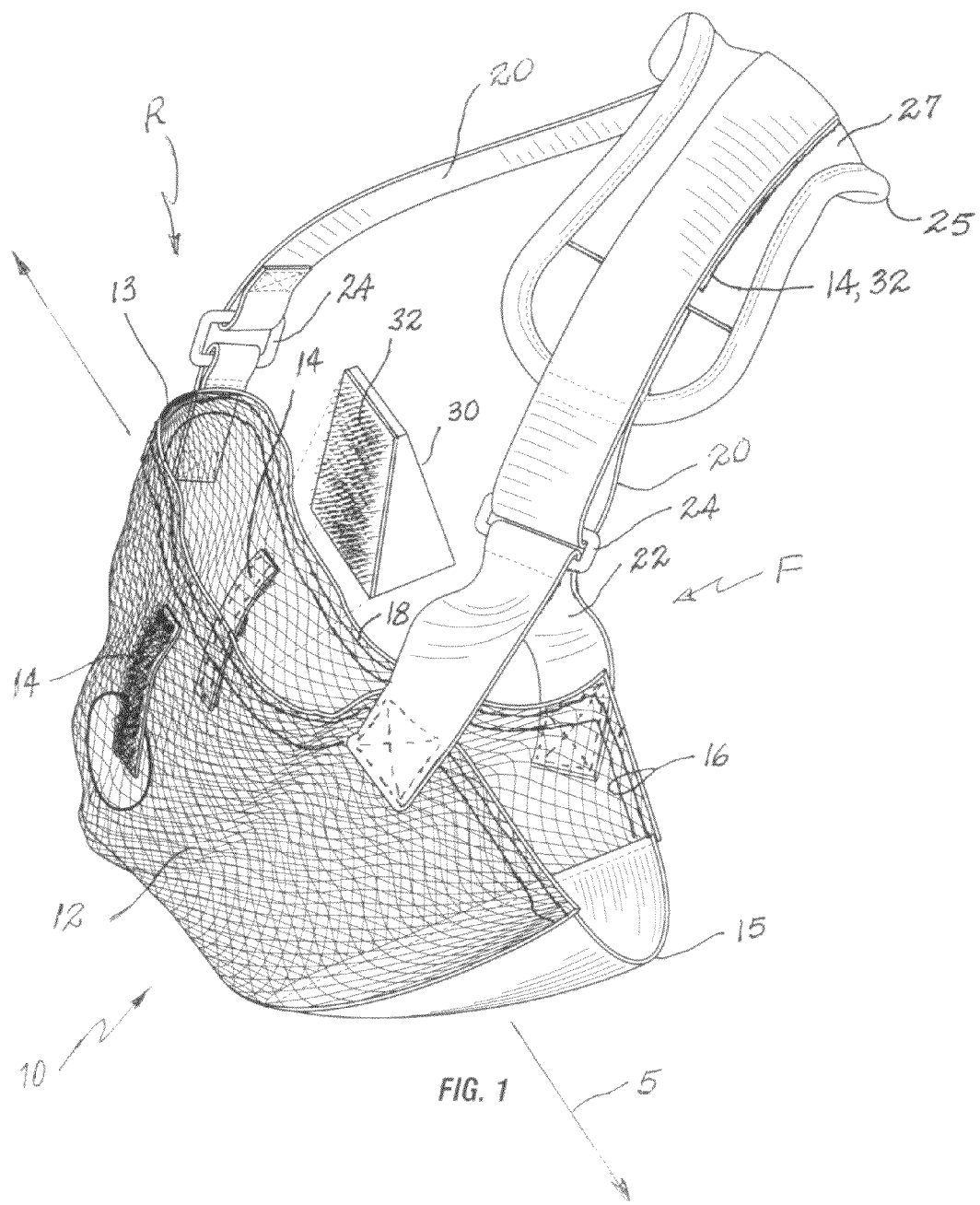
FIG. 1 is a perspective view of the presently described apparatus including a wedge shown separated from a sling to which it is attached to achieve anterior abduction of the sling and arm when the sling is supported by a shoulder strap.

The present invention is an arm support apparatus including a sling 10 which is generally configured in a V-shape with an open top about a longitudinal axis 5 as shown in FIG. 1. Fixed to an exterior surface 12 of the sling 10 are one or more first type of surface fastening means 14, referred to herein as patches 14 of loop type surface fastening material as shown, where two such patches 14 are shown fixed to opposing sides of sling 10. The patches 14 may also be hook type surface fastening material or any other first type of surface fastening means 14, as for instance eye hooks, zippers, buttons, and so on.

A shoulder strap 20 is engaged with the sling 10 and extends between a forward "F", and a rearward "R" engagement positions of the sling 10.

Figure 2:
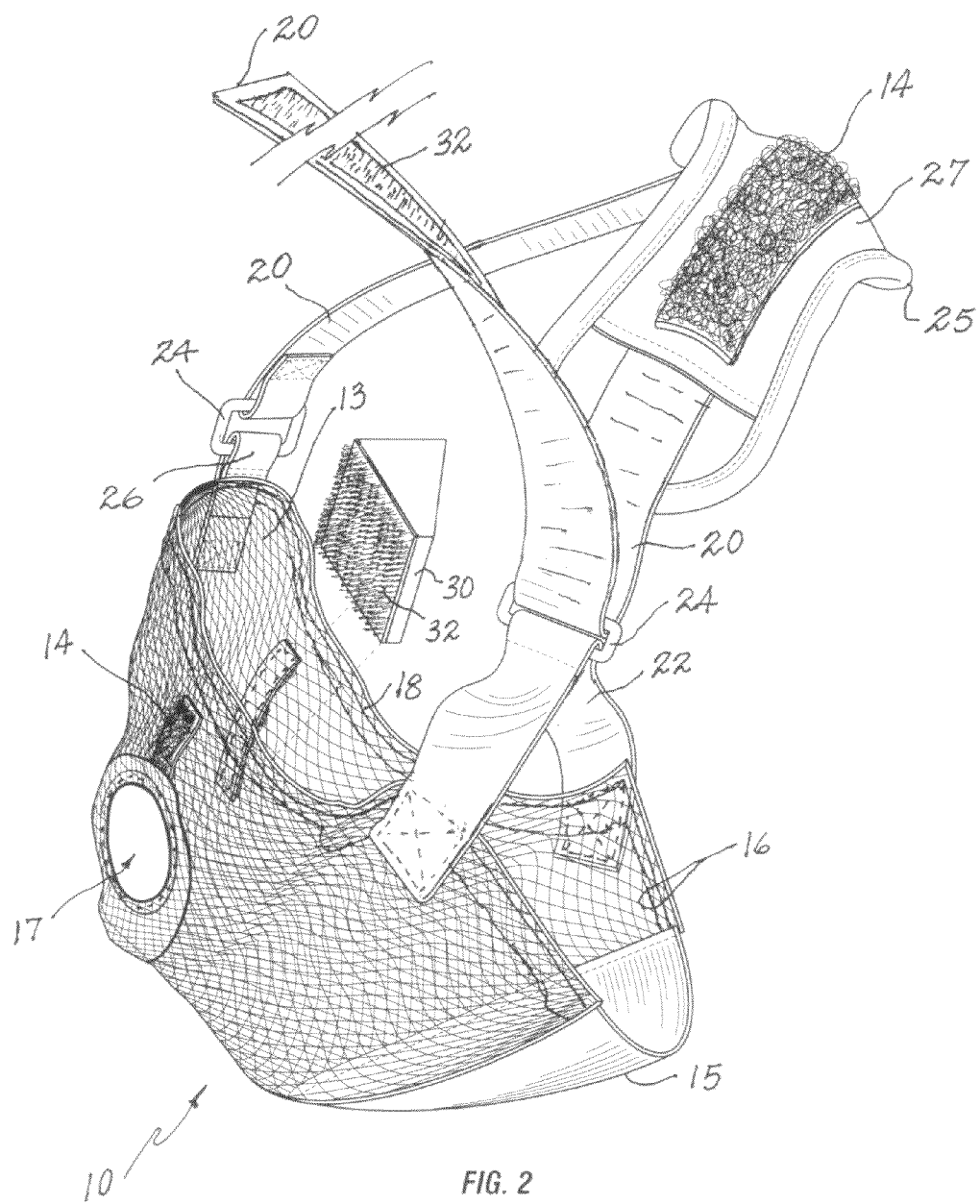
FIG. 2 is a further perspective view of the presently described apparatus including the wedge shown in FIG. 1 rotated for lateral abduction positioning of the sling when supported by the shoulder strap.

A positioning wedge 30 is made of a rubber or other compliant but relatively stiff substance and has a surface presenting a second type of surface fastening means 32, referred to herein as hook type surface fastening material 32, which also may be loop type fastening material or any other second type of surface fastening means 32 that is able to temporarily engaged and alternately disengage with one of the first type of surface fastening means 14. Clearly, as will be described, the positioning wedge 30 is mounted onto the exterior surface 12 of the sling 10 so as to produce the benefit of sling abduction, i.e., drawing the sling 10 away from the midline of the body. The first type of surface fastening means 14 is engaged with the second type of surface fastening means 32 thereby removably mounting the positioning wedge 30 on the exterior surface 12 of the sling 10. In FIGS. 1 and 2, the wedge 30 is shown separated from the sling 10, however, in use, the first and second type of surface fastening means 14 and 32 respectively join the wedge 30 on sling 10 so that with the wedge 30 in contact with the torso, the sling 10 is held away from contact with the torso and is oriented as desired. FIG. 1 shows the wedge 30 oriented so that the sling 10 is rotated away and upwardly with respect to a sling position that would be found if the wedge 30 were not inserted between sling 10 and the torso of the host. Likewise, in FIG. 2, wedge 30 is positioned so that the elbow of the host is moved away from the torso, that is lateral abduction.

The sling 10 is formed predominantly of a net material as shown in FIGS. 1 and 2, and this net material provides air circulation about a supported arm. The sling enables extension along its longitudinal axis 5, whereby the sling is able to be extended or shortened to fit a range of arm lengths. This is possible in that the net material has an open weave wherein nominally the woof (weft) and warp of the threads (yarns) of the net material form nearly squared rectangles. When it is desired to make the sling 10 longitudinally longer, this is accomplished by merely placing it in longitudinal tension whereby the rectangles move to a more trapezoidal shape elongating in the longitudinal direction and shortening in the cross direction. A hem 16 of the sling 10 extends around the upper edge of the sling 10 and contains an elastic strip 18. The net material is in a gathered state around the hem 16 of the sling 10 when the elastic strip 18 is unstretched. Therefore, when the elastic strip 18 is stretched longitudinally, the hem 16 is able to un-gather, allowing the sling 10 to elongate in the longitudinal direction.

A forward portion 15 of the sling 10 is constructed of elastic sheet material whereby a hand of a host using the sling 10 is elastically cradled. This is important in that the hand must not be placed subject to having its fingers entangled within the open weave spaces of the net fabric or supported less than over the hands full contact surface. The elastic sheet material is continuous offering no finger traps and is of such elasticity as to mold itself to the shape of the hand, thereby improving the overall support of the hand. The elastic sheet material terminates at the forward edge of the web material.

A rear portion 13 of the sling 10 contiguously joins opposing sides of the sling 10 as shown in FIGS. 1 and 2. Also shown in FIGS. 1 and 2 is that the sides of the sling 10 contiguously form a bottom portion of the sling 10. The sling 10 may provide a rearwardly positioned elbow hole 17 as best seen in FIG. 2 where a portion of the near sidewall of the sling 10 is cut away to reveal the elbow hole 17 which is useful for gripping the elbow in maintaining stability of the supported arm.

The shoulder strap 20 terminates forwardly at an inverted V-shaped attachment strap portion 22. Strap portion 22 is joined on both sides of sling 10 frontally and extends upwardly to join medially with a buckle 24 through which the shoulder strap 20 is slidingly engaged. The shoulder strap 20 terminates rearwardly joining with a linear attachment strap portion 26 at a further buckle 24 which is fixedly engaged with the rearward terminal end of shoulder strap 20. The linear attachment strap portion 26 is anchored terminally to the rear portion 113 of sling 10.

Figure 3:
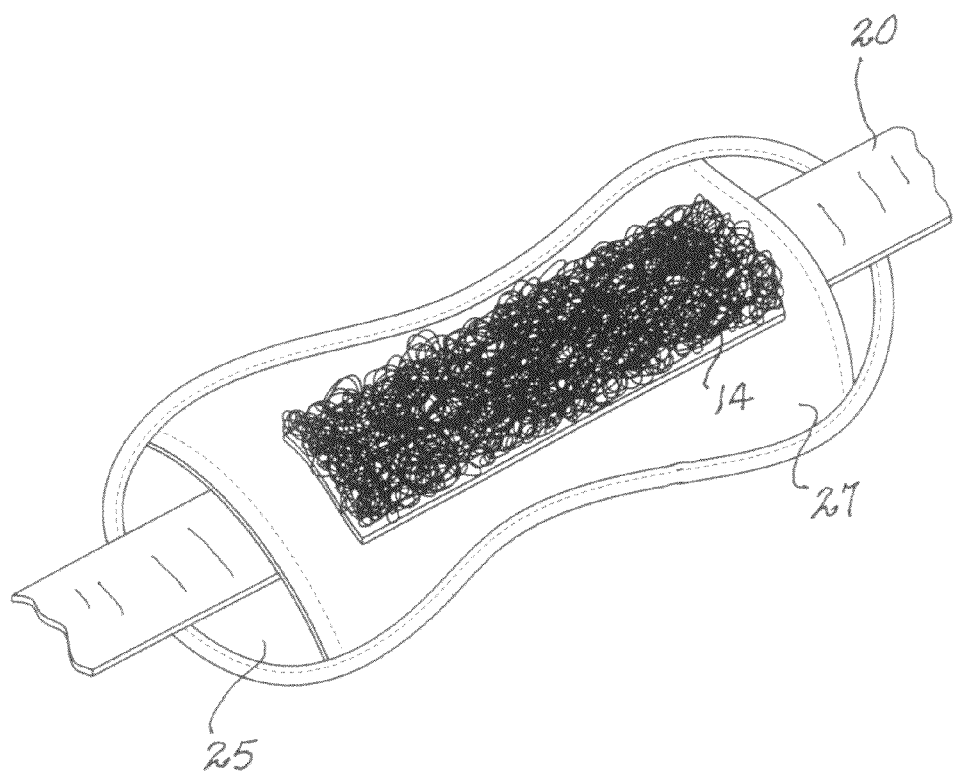
FIG. 3 is a perspective view of a shoulder pad of the invention showing a top surface of the shoulder pad as engaged with the shoulder strap.

A shoulder pad 25 of soft fabric is slidingly engaged with shoulder strap 20 as shown in FIG. 3. The pad 25 provides a sheath 27 within which strap 20 is engaged so that pad 25 is able to be moved along strap 20 to a most convenient and comfortable position. When strap 20 is mounted over the shoulder of a host, the pad 25 is preferably positioned on the top of the shoulder to prevent the strap 20 from pressing into the flesh. On the outside of sheath 27, a strip of the first type of surface fastening means 14 is attached. As shown in FIG. 2, strap 20 is drawn through buckle 24 adjacent to forward strap portion 22, and when the sling 10 is comfortably positioned, a length of the second type of surface fastening means 32 mounted on one side of strap 20 is pressed onto engagement with the first type of surface fastening means 114 as shown in FIG. 1. So it is clear from this that the strap sheath 27 and the shoulder strap 20 have a means for mutual gripping so as to secure the sling 110. Preferably the mutual gripping means is a hook and loop fastener arrangement as shown.

The enablements described in detail above are considered novel over the prior art of record and are considered critical to the operation of at least one aspect of the apparatus and its method of use and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that each named inventor believes that the claimed subject matter is what is intended to be patented.

What is claimed is:

1. An arm support apparatus comprising:
 a sling having a first type of surface fastening means attached on an exterior surface of the sling;
 the sling formed predominantly of a net material gathered on an elastic strip thereby enabling extension of the sling along a longitudinal axis of the sling, whereby the sling is able to fit a range of arm lengths;
 a second type of surface fastening means fixed to an exterior surface of a positioning wedge; and
 the first type of surface fastening means engaged with the second type of surface fastening means thereby removably mounting the positioning wedge on the exterior surface of the sling.

2. The arm support apparatus of claim 1 wherein a forward portion of the sling is made of elastic sheet material whereby a hand of a person using the sling is elastically cradled.

3. The arm support apparatus of claim 1 wherein a sheath and a shoulder strap have a means for mutual gripping.

4. The arm support apparatus of claim 3 wherein the mutual gripping means is a hook and loop fastener arrangement.

5. An arm support apparatus comprising:
 a sling having a first type of surface fastening means attached on an exterior surface of the sling, wherein a forward portion of the sling is made of elastic sheet material whereby a hand of a person using the sling is elastically cradled, the sling is formed predominantly of a net material gathered on an elastic strip thereby enabling extension of the sling along a longitudinal axis of the sling, whereby the sling is able to fit a range of arm lengths,
 a second type of surface fastening means fixed to an exterior surface of a positioning wedge;
 the first type of surface fastening means engaged with the second type of surface fastening means thereby removably mounting the positioning wedge on the exterior surface of the sling.

6. The arm support apparatus of claim 5 wherein a sheath and a shoulder strap have a means for mutual gripping.

7. The arm support apparatus of claim 6 wherein the mutual gripping means is a hook and loop fastener arrangement.

* * * * *